United States Patent [19]

Page et al.

[11] 4,432,968
[45] Feb. 21, 1984

[54] WEIGHT CONTROL WITH FAT IMBIBING POLYMERS

[75] Inventors: Judith L. Page; Daniel H. Haigh, both of Sanford; James Peters, Midland, all of Mich.

[73] Assignee: The Dow Chemical Company, Midland, Mich.

[21] Appl. No.: 313,052

[22] Filed: Oct. 19, 1981

Related U.S. Application Data

[63] Continuation-in-part of Ser. No. 198,687, Oct. 20, 1980, abandoned.

[51] Int. Cl.³ .................... A61K 31/78; A61K 31/74; A61K 31/745
[52] U.S. Cl. ........................................ 424/81; 424/78; 424/83
[58] Field of Search ............................ 424/78, 81, 83

[56] References Cited

U.S. PATENT DOCUMENTS

| | | | |
|---|---|---|---|
| 3,308,020 | 3/1967 | Wolf et al. | 167/65 |
| 3,520,806 | 7/1970 | Haigh | 210/40 |
| 3,750,688 | 8/1973 | Hall et al. | 137/2 |
| 3,780,171 | 12/1973 | Irmscher et al. | 424/79 |
| 3,787,474 | 1/1974 | Daniels et al. | 424/81 |
| 3,923,972 | 12/1975 | Fields et al. | 424/78 |
| 3,953,406 | 4/1976 | Marsh | 424/78 |
| 4,090,013 | 5/1978 | Ganslaw et al. | 424/81 |
| 4,115,550 | 9/1978 | Fields et al. | 424/78 |
| 4,211,765 | 7/1980 | Johnson et al. | 424/78 |
| 4,265,879 | 5/1981 | Fields et al. | 424/78 |

OTHER PUBLICATIONS

Chem. Abst. 78, 80342m & 80343n, (1973)–Dryden et al. & Cecil et al.
Chem. Abst. 83, 15572(a), (1975)–Marsh et al.
Chem. Abst. 87, 112,005(h), (1977)–Fischetti.

*Primary Examiner*—Douglas W. Robinson

[57] ABSTRACT

Pharmacologically-acceptable fat imbibing polymers are introduced into the gastrointestinal tract of animals to control body weight.

78 Claims, No Drawings

WEIGHT CONTROL WITH FAT IMBIBING POLYMERS

CROSS-REFERENCE TO RELATED U.S. APPLICATION

This application is a continuation-in-part of copending U.S. application Ser. No. 198,687 filed Oct. 20, 1980, now abandoned.

BACKGROUND OF THE INVENTION

1. Field of the Invention

This invention is concerned with the control of obesity by the introduction of certain fat imbibing polymers into the gastrointestinal tract.

2. Description of the Prior Art

Various polymers have been administered to animals to affect lipid (cholesterol) levels in the blood and liver. Many natural polymers, such as vegetable gums have been administered orally to reduce cholesterol levels. These materials have been reported to act by mechanisms such as increased degradation of cholesterol to bile salts, increased catabolism of cholesterol, and increased excretion of bile acids in fecal material, U.S. Pat. No. 4,175,124.

Synthetic polymers reported as lowering cholesterol levels include the quaternary ammonium styrene-divinylbenzene ion exchange resin, cholestyramine, U.S. Pat. Nos. 3,499,960 and 3,974,272;

a polymerized unsaturated carboxylic acid or anhydride or copolymer thereof with an unsaturated monomer. See, U.S. Pat. Nos. 3,923,972 (U.S. Pat. No. Re. 29,652) and 4,115,550, reporting increased excretion of cholesterol and fat, and diarrhea with severe weight loss in some cases, and weight control via inhibition of pancreatic lipase with certain cationic polymers of this group, in U.S. Pat. No. 4,211,765;

phenylene diamine ion exchange polymers, U.S. Pat. No. 3,980,770;

linear, unbranched, non-crosslinked polyamine resins as binders of bile acids, U.S. Pat. No. 4,027,009;

basic ion exchange resins, U.S. Pat. Nos. 4,041,153 and 4,064,234;

lightly crosslinked, swellable, water-insoluble polyurethanes, Marsh, U.S. Pat. No. 3,953,406, Marsh et al. JPL Quart. Tech. Rev. 2(4) 1–6 (1973), Chem. Abstr. 78:112334 d, and Marsh, JPL Quart. Tech. Rev. 1(1) 49–56 (1971), Chem. Abstr. 75:152435 g;

other crosslinked amine or ammonium polymers, U.S. Pat. Nos. 3,787,474, 3,780,171, 3,692,895.

A number of polymers have been described as useful in separating organic liquids such as fuels, oils, liquid hydrocarbons, by various mechanisms. These include organic liquid insoluble, organic liquid swellable alkylstyrene, organic-liquid-imbibing polymers, Haigh, U.S. Pat. No. 3,520,806;

non-ionogenic, non-swellable macroreticular adsorbing polymers, Gustafson, U.S. Pat. No. 3,531,463;

lightly crosslinked network polymers for absorbing oil and fat, Fletcher and Marsh, U.S. Pat. No. 4,039,489;

crosslinked urea formaldehyde or melamine formaldehyde resins in highly disperse form, U.S. Pat. No. 3,716,483; and, ion exchange resins, U.S. Pat. No. 3,729,410.

Various methods have been proposed for weight control to combat obesity. One of the more common methods is the use of relatively low-fat diets, i.e., diets containing less fat than a normal diet, although some fat is generally present even in diets considered relatively "fat-free". Fats are solids or liquid oils generally consisting of glycerol esters with higher fatty acids. Dietary sources of fats include both animal and vegetable fats, including predominantly triglyceride esters of both saturated and unsaturated fatty acids, as well as some free fatty acids. Glyceryl tristearate, glyceryl tripalmitate and glyceryl trioleate are among the most common esters.

Maintenance of fat-free or low-fat diets is difficult. The presence of fats in a great many food sources greatly limits the food sources which can be used. Additionally, fats contribute to the flavor, appearance and physical characteristics of many foodstuffs. Such factors adversely affect the acceptability of low-fat diets, and make the maintenance of such diets difficult.

Various chemical approaches have been proposed for controlling obesity. Anorectic agents, such as dextroamphetamine, are associated with undesired side effects. Indigestible materials such as mineral oil or neopentyl esters (see U.S. Pat. No. 2,962,419) have been proposed as substitutes for dietary fat. Diethylaminoethyl dextran, an ion exchange material, has been indicated to inhibit fat absorption in the body. Fischetti, Offenlegungsschrift 2,655,199, Chem. Abstr. 87:112005 h (1977). Garcinia acid and derivatives have been described as treating obesity by interfering with fatty acid synthesis. Swellable crosslinked vinyl pyridine resins have been described as appetite suppressants via the mechanism of providing non-nutritive bulk, U.S. Pat. No. 2,923,662. Cationic polymers such as dialkylaminoimides of alkene/maleic anhydride copolymers have been described as inhibiting pancreatic lipase, U.S. Pat. No. 4,211,765.

None of the above methods have been entirely satisfactory. Controlled diet remains the most prevalent technique for controlling obesity, with surgical techniques such as temporary iliary bypass surgery, being employed in extreme cases. It would be desirable to provide new means for controlling the weight gain producing effects of dietary fat.

SUMMARY OF THE INVENTION

This invention relates to a method for controlling the body weight of animals by administration of a polymer. More particularly, the invention is concerned with controlling the body weight of animals, including mammals, such as humans, by administering into the gastrointestinal tract an effective amount of an indigestible, pharmacologically-acceptable, fat imbibing, fat retaining polymer. The invention is also directed to the polymers useful for controlling the body weight of animals and pharmaceutical compositions thereof. More particularly, the invention provides a pharmacologically-acceptable, solid, particulate, crosslinked, indigestible, fat imbibing, fat retaining, polymer characterized in that it swells in liquid lard, contains less than 100 ppm of residual monomer and has a volume average particle diameter of from about 0.05 to about 2000 microns.

In accordance with the invention, it has been discovered that the administration of certain indigestible, pharmacologically-acceptable fat imbibing polymers into the gastrointestinal tract reduces the obesity inducing effect of the consumption of dietary fat. The polymers are capable of imbibing consumed dietary fat in the gastrointestinal tract, with the result that the imbibed fat and polymer are excreted without either the polymer or its imbibed fat being absorbed into the bloodstream.

The invention can thus be used for weight control in animals, that is, to control body weight, reduce body weight or reduce weight gain in animals, particularly animals consuming high fat foodstuffs or a high fat diet. It can be used to assist in weight maintenance with either obese or normal animals exposed to high fat foodstuffs or it can be employed as an aid to weight loss in obese animals.

In the method of the invention, an effective amount of one or more of the polymers of the invention is administered into the gastrointestinal tract of the animal in a manner effective to contact the polymer with fat in the gastrointestinal tract, either above or at a region or regions where fat absorption into the bloodstream occurs in the course of digestion. Preferably the compounds are administered orally, in admixture with the food or drinking water, or by separate oral administration, or by gavage. They can also be administered by intragastric intubation, or directly into the stomach or small intestine in fistulated animals, when appropriate. Oral administration is greatly preferred as it allows for contact of dietary fat and the compound in the stomach followed by continued contact in the small intestine where most metabolic fat absorption typically occurs.

It is critical that the polymer of the invention be administered in a manner effective to bring about the required contact of the polymer and ingested fat. This can be readily accomplished by administering the polymer at a time or times relative to the ingestion of at so as to ensure simultaneous presence of the polymer particles and ingested fat in the stomach or in the same regions of the small intestine, or both. In general, the polymer should be administered within one gastric residence time period before or after the consumption of fat, the absorption of which is to be controlled. The gastric residence time, i.e., the time between ingestion and passage of ingesta from the stomach into the intestinal tract, varies depending on known factors such as species, size, age and health of the mammal, feeding patterns, and type and quantity of ingested foodstuffs. In general, the gastric residence time for most mammals is between about one and about four hours. It is convenient and preferred to administer the polymer at a time or times between about one hour before and about one hour after feeding.

The polymers used in the invention are indigestible, pharmacologically-acceptable, solid, particulate, crosslinked, fat imbibing, fat retaining polymers which swell in liquid lard, contain less than 100 parts per million (ppm) of residual monomer and have a particle size of from about 0.05 to about 2000 microns ($\mu$). Advantageously, the polymer particle when swollen with liquefied lard has a volume of at least four times the initial (non-swollen) volume and contain less than 25 ppm of residual monomer, most preferably less than 10 ppm of residual monomer. The term "lard" in the context of this invention refers to the purified abdominal fat from a hog. The term "liquid lard" or "liquefied lard" refers to liquid lard near its melting point. In a preferred mode, the polymer particles, particularly those having a size of from about 0.05 to about 20 microns, have disposed thereon a surfactant (i.e., are at least partially coated with a surfactant).

The term "indigestible" is used herein to indicate that the polymers are not absorbed from the gastrointestinal tract, nor are they degraded or metabolized to an appreciable extent in the gastrointestinal tract to produce components which are absorbed. Thus, the polymers are also insoluble in the gastrointestinal liquids. They are insoluble in both the gastric fluid and bile produced by the animal. They are also insoluble in the ingesta, which can include both water and water miscible liquids such as glycerol as well as water immiscible liquids such as liquid dietary fats, fatty acids and edible oils, under the gastrointestinal tract conditions. The polymers are capable of remaining essentially undissolved throughout their passage through the gastrointestinal tract, and are not absorbed through the stomach or intestinal wall either as a solid or as a solution in the aqueous or fatty liquids which are absorbed in the digestive process. It is understood that the polymers are thus not degraded by acidic gastric fluid, or by digestive enzymes. They are not soluble in either gastric fluid or in the bile, nor are they solubilized by the surfactant action of the bile salts.

The polymers are also pharmacologically-acceptable, that is, they do not cause significant deleterious side effects which are unrelated to fat absorption by the polymers at dosages consistent with good weight control. The imbibition of fats by the polymers can directly effect factors such as blood lipid levels, generally in a beneficial manner. It can also decrease absorption of fat-soluble vitamins or drugs which may be dissolved in the liquids imbibed by the polymers, as well as absorption of nutritionally essential fatty acids, which are themselves imbibed. Such effects are directly related to fat absorption by the polymers, and can easily be controlled by appropriate dietary supplements and dosing schedules. Other side effects, such as irritation of the gastrointestinal tract, diarrhea or constipation, are neither necessary nor desirable for weight control, and it is a feature of the invention that the polymers employed are non-toxic and are relatively free of such side effects at dosages providing weight control.

Ionogenic polymers such as cationic or anionic ion exchange resins or polymers having a substantial amount of acidic or basic or other chemically reactive functional groups can interact or react chemically with the contents of the gastrointestinal lumen. Such interactions can produce side effects which are unrelated to fat imbibition. Accordingly the polymers should be essentially non-ionogenic, and be essentially chemically inert in the gastrointestinal tract for pharmacological acceptability. The polymers should also be essentially free of unreacted monomers, initiators, inhibitors, unreacted crosslinking agents or the like which are either biologically active or toxic, or chemically reactive with the ingesta. That is, the amounts of such substances should be low enough so that no detrimental side effects attributable to unreacted monomers, catalysts, etc., are obtained at dosages consistent with good weight control activity. In the polymer compositions, the presence of chemically reactive groups, whether on the polymer chain or present as unreacted materials from the polymerization, should be maintained at a pharmacologically-acceptable low level so that chemical or biological action or side effects of the reactive groups do not vitiate the fat imbibition and weight control.

The term "fat imbibing, fat retaining polymer" as used herein refers to those polymers which are insoluble in, but capable of absorbing and being swollen by dietary fat and retaining substantial amounts of the imbibed dietary fat under the conditions of the mammalian gastrointestinal tract. In other words, the polymers are swellable by a digestible dietary fat at physiologic temperatures and conditions in the gastric fluid or in both the gastric fluid and intestinal fluid and are capable of retaining the imbibed fats within the polymer particle both in the gastric environment and in the intestinal environment. In order to imbibe and retain dietary fat under the physiologic conditions of the digestive tract, the polymer must imbibe fats at a sufficiently high rate so that substantial amounts of fat are absorbed by the polymer before the fat is hydrolyzed or digested and absorbed by the animal.

The normal course of mammalian fat digestion and absorption is a complex physico-chemical process involving enzyme catalyzed hydrolysis of ingested triglycerides by several different lipases, with lipase introduction or lipolysis occurring in the pregastric phases (chewing and swallowing), in the acidic gastric juice, and in the more basic aqueous surfactant environment of the intestinal lumen. In the intestinal lumen, the dietary lipids can be involved in further lipolysis catalyzed mainly by lipase from the pancreas, formation of water soluble fatty acid soaps, emulsification and micelle formation with the aid of bile salts and biliary phospholipid surfactants such as lecithin. See, Borgström, Biblthca, Nutr. Dieta, vol. 25, pp 1-6, (1977). Bile (and even water) is known to be capable of extracting oils from certain oleophilic oil-imbibing polymers which are operable to imbibe oils in other environments, U.S. Pat. No. 3,953,406. Such release of fat can allow normal fat digestion to proceed. It is critical for the present invention that the polymer be both fat imbibing and fat retaining. The relative fat imbibing, fat retaining property of specific polymers can be investigated in vitro by conventional in vitro techniques using exposure to typical dietary fatty materials (such as melted butter, lard, vegetable oils, olive oil, edible fatty acids, etc.) in simulated gastric juice followed by exposure to simulated intestinal fluid, and measuring the amount of fat imbibed and retained, and the rate of imbibition. Polymers which absorb relatively insignificant amounts of fats within the gastric residence time for the animal species to be treated, or which readily release imbibed fats into simulated bile, will generally be of little or no value. However, due to the physicochemical complexity of the actual mammalian digestive process, and factors such as the number of fatty acids (typically 4, 6, 8, 10, 12, 14, 16, 18, 20 and 22 carbon atom linear fatty acids, each present in varying amounts), the effects of other ingesta in the diet, and the mechanical mixing of ingesta during mammalian digestion, it is generally more practical to carry out conventional range finding weight gain studies, or studies of post prandial blood lipid levels to ascertain the fat imbibing, fat retaining property of various polymers.

The stabilization and destabilization of suspensions follows the same principles as the stability of hydrophobic colloids with the additional complication that a stabilized suspension is influenced to a greater extent by gravitational effects of creaming or settling because of the larger size of their particles and the consequent relatively minor influence of Brownian motion in counteracting these effects. Thus, adding a dispersant which can adsorb on the particle surfaces and make them more hydrophilic or more highly charged with like charges can either reduce the attraction potential (van der Waals or London dispersion forces) or increase the repulsion potential (coulombic or electrostatic free energy of repulsion), leading to "stabilized suspensions".

Gravitational stabilization can be imparted to these suspensions by "thickening". Preferably, this can be accomplished by adding a material which causes an interaction leading to a network of particles inducing a structure, which can often be temporarily disrupted by shear to allow it to flow (thixotropy). Merely increasing viscosity by adding high polymers also retards the rate of gravitational separation. Soaps, detergents, anionic and cationic polyelectrolytes, proteins and nonionic polymers are useful in stabilization of suspensions. At higher concentrations or molecular weights, these can also act as thickeners or gravitational stabilizers.

This invention applies these principles to microsuspensions of imbibing polymers. It is illustrated using suspensions stabilized with a sodium salt of a fatty acid to give an anionic charge to the particles. Neutralization of this charge with acids destabilizes the suspension by making it hydrophobic, reducing the repulsion potential and inducing some particle aggregation for more rapid gravitational removal from the water. The reaction of the salt of the acid with acid, forms the free fatty acid which has a lower solubility and is not as effective as a stabilizer. The particles are then rapidly extracted from water into oils, where they can swell and imbibe the oil, making it unavailable for digestion. As the concentration of the soap is increased, the thickening of the suspension can be increased by particle interaction. Similar stabilization and destabilization effects would be expected with other carboxylic acids including polymeric acids where thickening effects could also be varied by molecular weight control and crosslinking.

This invention provides polymers which improve the rate of imbibition or gelation of oils and fats. The imbibition of oils and fats is important in the application of polymers to weight control and it has to do with the surface chemistry involved in the extraction of the polymer beads from the aqueous phase into the oil phase. The importance of the surface chemistry, i.e., the wettability of the polymer surface by oil or water, is indicated as follows: The beads had been rendered hydrophilic by using a hydroxypropyl methylcellulose (Methocel ®) stabilizer during polymerization. Washing off a part of the stabilizer improved both the extraction rate of the beads and the gelation rate of the fat in in vitro tests by making the suspension more hydrophobic. It was further shown that addition of a surfactant (sodium lauryl sulfate) in very small concentrations could completely stop the imbibing action of the beads for fats. These experiments showed that the hydrophilicity of the beads could interfere with their extraction into the oil phase by retarding their rate of removal from the aqueous phase.

The performance of these polymers is improved by making the beads more hydrophobic. This can be done by removal of more stabilizer, by drying or by partial flocculation to increase the particle size of the suspension; but is preferably done by using a dispersant, such as a fatty acid soap or other material based on a carboxylic acid, which would be hydrophilic at a pH closer to neutral than is stomach acid, and which would be rendered hydrophobic by destabilization at low pH, as in the stomach. This would then allow more rapid extraction of the beads from the aqueous phase into the oil phase and reduce the time for imbibition of the fat and the need for lengthy mixing and high dilution. Surfactants of low HLB (hydrophilic-lipophilic balance) are also useful, although these do not necessarily have the desirable, but not essential, property of dispersing in water and becoming hydrophobic when ingested. Flocculants, such as salts, or polymeric flocculants to increase rate of extraction by increasing particle size are also useful. Suitable surfactants include, for example, $C_8$ to $C_{18}$ saturated and unsaturated fatty acids such as stearic, palmitic, myristic, oleic and linoleic acids and their salts, such as the sodium, potassium, lithium, ammonium, calcium, magnesium or aluminum salts; $C_8$ to $C_{20}$ alcohols; polymers of carboxylic acids such as, for example, acrylic acid, methacrylic acid, maleic acid, fumaric acid and itaconic acid; and polydimethylsiloxane.

We have found that particles coated with stearic acid, either by dry mixing or precipitation from alcohol solution with water, gave improved extraction and imbibition rates. Using sodium stearate also gave improved rates when tested in acidic solution, but gave the additional advantages of improved dispersion of the filter cakes for resuspension and a thickening action to prevent creaming (i.e., layering of the polymer particles near the surface) of the beads in water. Using a salt of an acid which becomes insoluble or hydrophobic when neutralized with an acid allows the beads to be dispersed in water when the salt form is present, but to be rapidly extracted into the oil phase when the acid form is made by reaction with acid, provided in this application by the gastric juices present in the stomach.

Using a surfactant of hydrophobic nature to make the surface of the particles hydrophobic without relying on a change of pH is illustrated by the work with particles coated with stearic acid directly. The same result is found with other hydrophobic surfactants such as sorbitan monolaurate.

Making a hydrophilic material hydrophobic can also be accomplished by reaction of the anionic carboxylic salt with multivalent ions such as $Ca^{++}$, $Mg^{++}$ or $Al^{+++}$.

When food is ingested, fats are retained in the stomach for a long time relative to the water-soluble or water-dispersed fraction of the stomach contents. The objective is to absorb these fats during the time that they are in the stomach, using fat imbibing polymers for this purpose. The polymers containing the imbibed fats will then pass through the digestive system retaining the imbibed fats in opposition to the natural absorption processes of the body. Of these, that which most concerns us is the presence of a natural surfactant system in the digestive tract, the bile salts. Their function is to aid in the emulsification of fats and other lipids in the duodenum. At high enough concentrations however, the bile salts can also prevent the absorption of fats by polymers which can normally imbibe them. Since these bile salts are not normally present in the stomach, the imbibition of fat by the polymers is more likely to occur there than in the duodenum, although absorption of fat by polymer there is not excluded.

The presence of other materials with a surfactant nature can also retard the absorption of fats in the stomach by altering the wettability of the polymer. The polymer must come into contact with the fat in order to swell; it should not be wet by water so that it is retained in the aqueous phase. Surfactants which are oil-wet can accelerate the transfer of polymer from the aqueous phase into the oil phase so that the imbibition can begin sooner and so that the polymer is retained in the stomach along with the fat, rather than being transported out with the aqueous phase.

Lightly crosslinked oil-swellable polymers are known to imbibe hydrocarbons and oils but it is not obvious that these polymers can imbibe fats from the contents of the digestive tract, or that the polymers can retain these fats in competition with the normal mechanisms of digestion. Bile salts, fatty acids, glycerides and phospholipids can emulsify fats and retain them in micelles in the aqueous phase of the intestinal contents, making them unavailable for absorption by polymers and even extracting the fats from the polymer after they have been imbibed in the polymer prior to contact with the bile salts. Results of this nature have been reported by Marsh & Wallace (JPL Quart. Tech. Rev., Vol. 2, No. 4, pp. 1–6 (1973)) and led them to develop polymers which could absorb these bile lipids. Their polymers contain both hydrophilic and hydrophobic parts so that they can absorb both water and oil and thus remove the lipid molecules which are contained in the aqueous phase of the intestinal contents.

The polymers proposed by Johnson & Fields (U.S. Pat. No. 3,923,972, December, 1975; U.S. Pat. No. 4,115,550, September, 1978; and U.S. Pat. No. 4,211,765, July, 1980) for controlling obesity also work by an entirely different mechanism. These are copolymers of a carboxylic acid monomer (e.g. maleic anhydride or acid) and an alkene. The polymers are not necessarily crosslinked and are water-soluble when not crosslinked and water-swellable if crosslinked. Their action interferes with the action of pancreatic lipase; they do not imbibe fats and hold them unavailable for digestion. The polymers proposed by Johnson & Fields interfere with the digestion of fats by making their breakdown impossible because of the inactivity of the needed enzyme.

The indigestible, pharmacologically-acceptable, fat imbibing, fat retaining polymers employed in the invention are solid, particulate, including reticulate particles, lightly crosslinked copolymers of, for example, isobornyl acrylate, isobornyl methacrylate, sytrene or alkylstyrenes (preferably tertiary-alkylstyrenes wherein the alkyl groups contain from 4 to 12 carbon atoms) and one or more alkyl ester of a $C_1$ to $C_{20}$ alcohol and acrylic or methacrylic acid. The alkylstyrene can be, for example, 4-tert-butylstyrene, 4-tert-amylstyrene, 3,5-ditert-butylstyrene, 4-tert-hexylstyrene, 4-tert-octylstyrene or 4-tert-dodecylstyrene. Tertiary-butylstyrene (4-tert-butylstyrene "TBS") is the preferred alkylstyrene. The alkyl ester monomers can include, for example, butyl methacrylate, butyl acrylate, hexyl acrylate, 2-ethylhexyl acrylate, cetyl methacrylate, eicosyl acrylate, the mixed ester cetyl-eicosyl methacrylate, lauryl methacrylate, stearyl methacrylate or lauryl acrylate. The alcohol moiety of the ester is preferably of 8 to 20 carbon atoms, and is preferably a linear fatty alcohol residue, such as cetyl, lauryl, stearyl or eicosyl, or a secondary alcohol residue.

The alkylstyrene should be the predominant monomer, the copolymer containing at least 50 percent by weight, and preferably from about 60 to about 85 to 90 percent by weight of the alkylstyrene. The alkyl ester monomer preferably includes both a methacrylate ester and an acrylate ester of one or more $C_8$ to $C_{20}$ fatty alcohols, or a $C_8$ to $C_{20}$ fatty alcohol methacrylate or acrylate as essentially the sole comonomer.

The copolymer is preferably lightly crosslinked to insure that the polymer will not be soluble in or miscible with dietary fats and oils. Too much crosslinking, i.e., 0.5 percent by weight or more, will hinder or prevent the polymer particles from imbibing fats. In general, the preferred polymers can contain from about 0.001 to about 0.1 percent by weight of a crosslinking agent (based on the total weight of the alkylstyrene and alkyl ester monomers). Preferably, about 0.01 to about 0.075 percent of crosslinking agent is employed. The crosslinking agent can be any di- or polyfunctional compound known to be useful as a crosslinking agent in polymeric vinyl addition compositions, such as divinylbenzene, vinyl isopropenyl benzene, butadiene, or other polyethylenically unsaturated crosslinking agents described, for example, in U.S. Pat. No. 3,520,806. Divinylbenzene is preferred as a crosslinking agent, in amounts from about 0.025 to about 0.05 to about 0.075 to about 0.1 weight percent.

The polymers can be administered in any pharmaceutically-acceptable form, that is, in any physical form in which the polymer can be conveniently introduced into the gastrointestinal tract in a manner which allows sufficient contact of the polymer and dietary fat, and in which the physical form of the polymer particles themselves do not cause significant irritation of the intestinal wall or other deleterious side effects which would vitiate the beneficial effects of the invention. Preferably, the polymers are employed in the form of small particles, such as granules, powders, beads, or small spherical particles sometimes referred to as "microspheres".

The size of the polymer particles is related to their ability to absorb dietary fat. In general, for a given amount of polymer administered, the contact with dietary fat and rate of fat absorption is enhanced as the ratio of surface area to weight of the polymer increases. Thus smaller particles, with diameters such as from 100–500 Angstrom units to 5 microns, generally imbibe fat more rapidly and are generally more effective on a weight basis than particles from 5 to 50 microns in diameter, which are, in turn, more effective than particles in the 50 micron to 1 to 2 millimeter range, and so on up to the maximum size conveniently administrable for the animal species in question.

Particles with an average diameter of about 30 to 60 microns or greater are difficult to maintain in aqueous suspension. They are large enough to be detectable by most mammals during oral administration, having an undesirable sandy or gritty texture which makes oral administration difficult unless the particles are enclosed in a capsule or the like to prevent a mass of large particles from contacting the inside of the mouth. Accordingly, particle sizes below about 50 microns are preferred, and preferably the particles are sufficiently small to form a stable aqueous dispersion.

The polymer particles must also be of sufficient size to prevent passage of significant amounts of particles into or through the intestinal wall, therefore preventing the distribution of particles in other parts of the body, such as the blood stream. Significant migration of polymer particles through the intestinal wall can lead to their accumulation in other parts of the body, with deleterious side effects. The exact lower size limit to be employed in particular cases can be ascertained by conventional range finding studies such as using radioactive labelled polymers, for example, to ascertain the fate and distribution of the particles. In general, all the particles should be greater than about 40 Angstrom units in their smallest dimension and desirably at least 1000 Angstroms units wide at their smallest dimension. It is convenient to employ generally spherical particles which have diameters of from about 0.05 to about 20 microns. It is preferred to employ such particles with diameters from about 0.5 to about 20 microns.

The small particles can be prepared by a variety of known methods such as grinding, milling, cutting or comminuting extruded strands of polymer, or by emulsion or suspension polymerization techniques. Various techniques are disclosed in U.S. Pat. Nos. 3,615,972 and 4,071,670. Suspension polymerization is a well known process for forming polymer particles with spherical or bead-like configuration and relatively uniform particle size, and this technique can be conveniently employed to make the polymers.

The polymers are preferably, but not necessarily, prepared by emulsion or suspension polymerization of the monomers (and crosslinking agent) in an aqueous emulsion or aqueous suspension. In emulsion polymerization, the polymerization occurs in micelles formed by the monomer mixture and the emulsifier. In the suspension technique, polymerization occurs in monomer droplets suspended in the aqueous phase. Suspension polymerization is preferred for making larger particles, e.g. from about 0.3 to 0.5 micron and larger.

The polymerization reaction proceeds at temperatures from about 50° to 120° C., conveniently from 70° to 90° C., and in the presence of a minor amount (typically from about 0.5 to 10 times the amount of the crosslinking agent) of a polymerization initiator such as potassium persulfate or tertiary-butyl peroctoate. In preparing the copolymers, the monomers and crosslinking agent are mixed together, in the proportions corresponding to those desired for the product, then dispersed in water containing either an emulsifying agent or a suspending agent. The proportions are preferably selected so the monomer plus crosslinking agent comprises about 20 to about 60 percent by weight of the aqueous mixture. The polymerization initiator is mixed with either the monomer mixture or the aqueous phase depending on the polymerization method, the initiator used and its relative solubility in the two phases. The mixture is then mixed, e.g., with a high-shear mixer or a homogenizer, to disperse the monomer phase in the aqueous phase, and to reduce the particle size of the mixture of monomer and crosslinking agent to the size desired for suspension polymerization; and to form micelles of the desired size for emulsion polymerization. The resulting mixture is heated with stirring at a temperature in the polymerization temperature range until the reaction is substantially complete (generally 4 to 24 hours). The copolymer product can be recovered and worked up by conventional techniques such as filtration or screening to remove any coagulum or large-particle waste, dialysis, lyophilization or, particularly, with polymer particle sizes on the order of 0.15 micron and larger, by filtration to separate the reaction medium, alcohol precipitation, washing with lower alkanols, steam distillation or other known techniques.

In a convenient purification procedure for polymer particles prepared by suspension polymerization, the suspension is passed through a screen to remove any large coagulum waste particles, then mixed with about 10 parts by volume of isopropanol. The particles are allowed to settle, and the supernatant liquid removed by decantation. Washing with isopropanol can be repeated, if desired. The washed polymer particles can be separated by conventional techniques such as decantation, centrifugation, evaporation, or filtration. The washed particles can be used directly, or suspended in an aqueous carrier.

Purification is preferably achieved by isolating the material as a filter cake and then sequentially washing the intact filter cake with deionized water and then an alcohol such as, for example, 190 proof ethanol or isopropanol, under pressure.

In using the polymers of the invention, the polymers are preferably administered as formulations in admixture with a pharmaceutically-acceptable carrier, which can be one or more conventional pharmaceutical excipients which are physically and chemically compatible with the polymer and which are non-toxic and without deleterious side effects to the animal being treated under the conditions of use. In general, aqueous pharmaceutically-acceptable carriers, such as water or aqueous dilute ethanol are preferred. Such formulations can include flavoring agents such as sucrose, fructose, invert sugar, cocoa, citric acid, ascorbic acid, fruit juices, vegetable juices, etc. In general, digestible oil or fat based carriers should be avoided or minimized as they contribute to the condition sought to be alleviated by the use of the polymers. Digestible oil or fat based carriers are also subject to absorption by the polymers during prolonged contact, thus reducing the capacity of the polymer to absorb dietary fats after administration.

The polymers can be prepared as concentrates, for dilution prior to administration, and as formulations suitable for direct oral administration. They can be administered orally ad libitum, on a relatively continuous basis, for example, by dispersing the polymer in the drinking water. In one preferred embodiment, the polymer compositions are administered in the form of dosage units, each such dosage unit comprising a pharmaceutically-acceptable carrier and an effective dosage of the polymer sufficient to absorb a substantial amount of the dietary fat normally consumed by the animal at a single feeding. A preferred group of pharmaceutically-acceptable carriers, particularly when employing polymers having a large particle size, i.e., 10 microns or larger, comprises the pharmaceutically-acceptable suspending agents such as hydroxypropyl methylcellulose, carboxymethyl cellulose, pectin, tragacanth and the like. When polymers having a smaller particle size are employed it is desirable to use a suspending agent having a lower HLB or one which converts to having a low HLB in the stomach such as, for example, sodium stearate. In the case of animals which consume dietary fats at several different feedings per day, it is convenient to administer separate dosage units in conjunction with each feeding or with at least one or more of the individual feedings. Dosage units will generally contain from about 250 milligrams or less to about 60 grams or more of polymer per unit. Preferred dosage units are gelatin capsules containing solid particulate polymer and individual units of an aqueous suspension of the polymer containing a pharmaceutically-acceptable suspending agent.

In the following examples all percentages are by weight unless otherwise specified.

EXAMPLE 1

Tertiary-butylstyrene-based polymer beads ("Imbiber Beads", The Dow Chemical Company, Midland, Michigan) being a terpolymer of 70 percent (%) t-butylstyrene, 20% 2-ethylhexyl acrylate and 10% cetyleicosyl methacrylate (weight percent) with 0.05% divinylbenzene (DVB) as a crosslinking agent were evaluated in beagle dogs. The TBS polymer beads were in the form of solid beads with particle size distribution from 50 to 450 microns in diameter. The beads were administered orally in ⅛ ounce gelatin capsules, approximately 1.5 grams (g) of TBS polymer beads per capsule.

Separate groups of male beagle dogs were administered a high fat diet made up of 33.2% laboratory dog chow (Purina ®), 8.3% non-fat powdered milk solids, 7.1% canned beef dog food (Fromm ®), 18.1% lard and 33.3% water. The dogs were separately caged, and each dog was fed once daily a one pound portion of the above diet mixture with water ad libitum. The caloric content of each one pound diet portion was 1445 calories of which about 59%, or approximately 850 calories, was dietary fat (about 91 grams of fat). This calorie content was two to three times that needed for maintenance.

The dogs in the test group were administered 7.5 grams of polymer beads per dog per day, by oral administration in five gelatin capsules. The capsules were administered 30 minutes before feeding. This dosage amounts to about 1.6% of the diet or about 8% based on the daily fat consumption. Dogs in the control group were similarly fed, and were similarly administered five, ⅛ ounce, empty placebo gelatin capsules.

After three months, it was visually apparent that the dogs of the control group were gaining weight more rapidly than the dogs receiving the polymer beads. The mean body weight in kilogram ($\pm$standard deviation) in the control group increased from 9.7$\pm$0.7 kilograms (kg) initially to 13.8$\pm$0.3 kg after twelve weeks. In the treated group the initial mean body weight was 9.9$\pm$0.2 kg, and the 12 week weight was 12.3$\pm$0.5 kg. After six months the control dogs were markedly obese, with subdermal layers of fat obscuring the backbone and ribcage. The polymer treated dogs were beginning to show signs of obesity at six months, but visibly less than the control dogs. The mean body weight in the control group at six months was 16.3$\pm$1.4 kg as compared to 14.5$\pm$0.5 kg in the treated group. One dog in the treated group varied its eating pattern beginning in about the eighth week, to take increasingly longer periods (up to 24 hours in the sixth month) to consume its diet portion, thus eating significant amounts of food more than one gastric residence time after dosing. This dog was found to have gained more weight (5.1 kg vs. 4.3 kg) than the other treated dogs. The findings with this dog indicate the effect of administering the polymer more than one gastric residence time from the consumption of food.

Analysis of serum cholesterol levels indicated no significant differences throughout the study. Fasting levels of serum triglycerides and liver triglycerides did not appear significantly different. Serum triglycerides levels on two-hour post prandial samples were reduced significantly in the polymer treated dogs, indicating reduced triglyceride absorption from the gastrointestinal tract. Observations during necropsy indicated no adverse effects attributable to the polymer beads, but did indicate increased adipose tissue in the mycocardium and within skeletal muscle in the control dogs receiving the high fat diet and no polymer beads. Marked excess subcutaneous and abdominal adipose tissue was observed in the control dogs and the treated dog which varied its eating pattern.

EXAMPLE 2

Polymer beads (20% by weight cetyl-eicosyl methacrylate-80% tertiary-butylstyrene lightly crosslinked with 0.07% divinylbenzene) were evaluated in rats. Separate groups of rats were fed for four weeks on a conventional laboratory rat chow ration, either unsupplemented (normal diet); or supplemented with 5 percent chloesterol and 1% cholic acid (high cholesterol diet). Other groups of rats were fed either the normal diet or high cholesterol diet mixed with 1% or 2% of the polymer beads.

The polymer bead treatment appeared to reduce serum cholesterol levels in comparing the normal diet and normal diet plus beads groups, but no decrease was observed in comparing the high cholesterol diet groups. The mean body weights after four weeks were less in the groups of rats receiving the beads in both the normal and high cholesterol diet groups. The mean four week body weights in the normal and high cholesterol diet groups were 335 and 340 grams; in the normal diet 1% and 2% bead groups 327 and 323 grams, and in the high cholesterol diet 1% and 2% bead groups 325 and 319 grams.

EXAMPLE 3

Polymer suspensions resembling latex polymer suspensions were prepared as follows:

In the following operations, monomers are purified before use by passing them through a bed of activated alumina to remove polymerization inhibitors.

A. t-Butylstyrene, 2-Ethylhexyl Acrylate Lauryl Methacrylate Terpolymer (Lightly Crosslinked)

A two gallon capacity reactor was charged with 2160 grams deionized water, 2.56 grams potassium persulfate (polymerization initiator), 5.04 grams sodium bicarbonate (pH buffer) and 46.96 grams of aqueous 30 percent Duponol® WN surfactant (a sodium mixed long chain alkyl sulfate). The mixture was heated to 80° C., with agitation; and 94 grams of a monomer mixture were added over a 90 minute period. The monomer mixture was prepared by mixing 1120 grams t-butylstyrene, 320 grams 2-ethylhexyl acrylate; and 1.43 grams divinylbenzene (crosslinking agent). The resulting mixture of initial charge and the 94 grams of the monomer mixture was allowed to react for one hour after the addition was completed. A homogenized mixture of 160 grams lauryl methacrylate and 320 grams of aqueous 0.6 percent Duponol® WN solution was added rapidly; after which continuous addition of both the balance of the monomer mixture (288 grams/hour) and an aqueous mixture (264 milliliters/hour) was started. The aqueous mixture was 100.3 grams of aqueous 30% Duponol® WN, 9.87 grams sodium bicarbonate, and b 5.12 grams potassium persulfate in 1120 grams of deionized water. Mixing and heating at 80° C. was continued during these additions (about 4.5 to 5 hours). The mixture was then heated at 90° C. for one hour, and then filtered through a screen with 40 meshes to the inch, which retained about 0.5 gram coagulum waste with a total "wet" waste of 11.5 grams. The filtered polymer suspension (yield 98.7%) contained 31.1% solids. The particle size was determined by light scattering to be 1420 Angstrom units. The copolymer of t-butylstyrene (about 70%), 2-ethylhexyl acrylate (about 20%), and lauryl methacrylate (about 10%), crosslinked with divinylbenzene (about 0.01%) was administered to animals on a high fat diet as described in Example 4 below.

B. t-Butylstyrene (70%)-Lauryl Methacrylate (30%) (Lightly Crosslinked) With About 0.05% Divinylbenzene 175 Grams of t-butylstyrene and 75 grams of lauryl methacrylate were mixed together. 0.227 Gram of divinylbenzene crosslinking agent [Divinylbenzene 55, (55% active divinylbenzene) The Dow Chemical Company, Midland, MI 48460, USA] and 0.5 gram t-butyl peroctoate initiator were mixed with the above monomer mixture to form an oil phase mixture. Separately, 10.8 grams hydroxypropyl methylcellulose (Methocel K-3, The Dow Chemical Company, Midland MI 48640, USA) was dissolved in 292 milliliters (ml) deionized water to make an aqueous phase mixture.

The resulting oil phase and aqueous phase mixtures were combined and mixed with a high-shear Eppenbach mixer (Admiral Tool & Die, Inc. Long Island City, N.Y.) at 5800 revolutions per minute (rpm) for 5 minutes. The resulting presuspension was transferred to a one-liter reactor flask, and heated for 16–20 hours at 70°–75° C. under a nitrogen blanket, with constant mild agitation (to ensure heat transfer). The mixture was then allowed to cool to ambient temperature, and was filtered through a 100 mesh screen. In the resulting aqueous latex-like polymer suspension the polymer particles had a volume average diameter of 4.84 microns, with a geometric standard deviation of 1.38.

C. t-Butylstyrene (70%), Stearyl Methacrylate (30%) (Lightly Crosslinked) with 0.05% Divinylbenzene In a similar procedure to that of Example 3B, 166.25 grams t-butylstyrene and 83.75 grams stearyl methacrylate were mixed, then mixed with 0.227 gram divinylbenzene and 0.5 gram t-butyl peroctoate to prepare an oil phase mixture. A water phase mixture was prepared by dissolving 8.13 grams hydroxypropyl methylcellulose in 292 ml of deionized water. The oil phase and water phase mixtures were combined and mixed, and the polymerization carried out as in Example 3B. The resulting lightly crosslinked t-butylstyrene-stearyl methacrylate copolymer latex-like suspension particles had a volume average diameter of 5.55 microns with a geometric standard deviation of 1.64.

EXAMPLE 4

Four groups of rats were fed on a diet of standard rodent chow plus 10 percent lard (high fat diet). Three of the four groups were administered one milliliter doses of the separate polymers of Example 3 (A, B and C) in aqueous suspension form, three doses daily, intragastrically by gavage. The fourth group was administered similar dosages of water to serve as a high fat diet control. A fifth group of rats was similarly dosed with water and fed the normal basal rat diet, rather than the high fat diet. Animal weight and food intake rates were recorded, and weekly weight gains in the five groups were studied for 21 days. The average food intake per rat per day was between 25.6 and 26.9 grams, and did not differ significantly from group to group. The weekly weight gains measured in the basal diet control group and the three high fat diet groups dosed with one of the polymers A, B and C were not significantly different. The three week weight gain average for the basal control group was 33.75 grams, for the high fat/copolymer A group 36.00 grams, for the high fat/copolymer B group 34.27 grams, and for the high fat/copolymer C group 38.55 grams. In contrast, the high fat diet control group had an average weight gain of 57.36 grams which was significantly higher than the weight gains in each of the other groups. This group also had serum cholesterol levels significantly higher than any of the other four groups. The serum cholesterol levels in the basal diet control group and the three polymer treated groups were not significantly different.

EXAMPLE 5

A study was carried out using a solid, large (on the order of about 150 microns average diameter) bead form, prepared by conventional suspension polymerization, and a liquid, small bead form (resembling a polymer latex) of a copolymer of 70% TBS, 20% 2-ethylhexyl acrylate and 10% lauryl methacrylate crosslinked with about 0.05% DVB. The liquid dispersion was prepared by an emulsion polymerization process similar to that of Example 3A, giving particle diameters on the order of 0.15 micron.

Groups of 12 male Wistar rats each were used in this study. Test groups included a basal diet (normal rat feed + 2.5% added sucrose); control group; a high fat (10% added lard + 2.5% sucrose) control group; a group fed high fat + sucrose diet and administered 310 milligrams (mg) of the solid form of the large beads twice daily; and a group fed the high fat + sucrose diet and administered orally an equivalent volume to equal 310 mg of the solids in the polymer latex-like liquid. The study was of a 32 day duration. During the first 11 days of the study, both the rats given the solid beads and the rats given the polymer liquid dispersion showed a slight weight gain suppression and a slight decrease in food consumption. However, by test day 14 the food consumption of both groups was comparable to that in the high fat control group. Review of the data for the entire 32 day period indicated that starting on test day 14 and thereafter the liquid dispersion rats had significantly decreased weight gains compared to the high fat diet control group and were comparable to the basal diet group (about 30 grams body weight less than the high fat diet control group after 32 days). The solid bead treated rats showed no significant differences in weight gains when compared to the high fat diet group. In addition, there were no significant differences in mean food consumption averaged over the entire 32 day test period between the high fat group and all the copolymer treated groups; however, there was a significant difference between the high fat and basal control groups. Selected rats from each group were submitted for gross necropsy examination. No lesions were found. Visual examination of the stomach contents revealed that the latex like liquid dispersion form of the copolymer was well dispersed in the ingesta, whereas, the beads administered in solid form appeared to be layered in the ingesta, thus resulting in less contact between the beads and ingested dietary fat than was obtained with the liquid polymer latex-like dispersion form. This illustrates the importance of obtaining good contact between the polymer particles and ingested fat in the gastrointestinal tract, and the good results obtained with the small particles in the aqueous dispersion form.

EXAMPLE 6

The polymer suspension of Example 3A (70% TBS, 20% 2-ethylhexyl acrylate, 10% lauryl methacrylate, lightly crosslinked with 0.05% divinylbenzene, spherical particle diameter about 0.15 micron, was employed in another operation using rats.

Separate groups of male rats (average weight 370 grams) were fed on different regimens using either a control diet consisting of standard laboratory rodent chow or a high fat diet consisting of 87.5% control diet chow mixed with 2.5% sucrose and 10% lard. Four groups of 12 rats each were allowed to feed during an 8 hour period each day, and were orally administered two daily dosages of either 1 ml water or 1 ml of the polymer suspension (30% solids). The first dose was given at the beginning of the feeding period, and the second dose four hours later. The four groups were the following: control diet-water, high fat diet-water, control diet-polymer, and high fat diet-polymer.

After 21 days, the average body weights of the control diet-polymer and high fat diet-polymer groups were 405 and 414 grams per rat, respectively, and were not statistically significantly different from the control diet-water group average weight of 408 grams/rat. In contrast, the average weight of the high fat diet-water group was significantly higher; 434 grams per animal. During the study, some rats died from physical injury to the esophagus or stomach wall while struggling during the intubation dosing process. Two such deaths occurred in the control diet-water group, and three deaths each in each of the other three groups.

EXAMPLE 7

A copolymer microsuspension was prepared by suspension polymerization. The copolymer particles were a copolymer of 70 percent (by weight) t-butylstyrene and 30 percent (by weight) lauryl methacrylate lightly crosslinked with 0.075 percent (by weight based on total of the two above monomers) divinylbenzene. The t-butylstyrene employed as radiolabeled with Carbon-14 at the $\beta$-carbon of the t-butylstyrene. The copolymer had a volume average particle size of 5.1 microns (volume average spherical particle diameter), and a specific radioactivity of 0.054 microCuries per milligram.

The copolymer was purified by washing with isopropanol, and was resuspended in aqueous 3.3 percent hydroxypropyl methylcellulose (Methocel K-3, Dow Chemical U.S.A., Midland, MI) at a concentration of 36.08 percent solids (by weight). The radiochemical purity of the resulting material was estimated to be greater than 99.9 percent.

A single oral dose of the above copolymer suspension was administered orally to rats in two groups. One group consisted of normal rats; the second group consisted of bile-cannulated rats with a surgically implanted bile duct cannula so that bile was excreted through a biliary fistula. The rats were each administered a single oral dose of 500 milligrams of the radiolabeled copolymer per kilogram of body weight, in a volume of 1.4 ml/kg with a radioactive dose of 27 microCuries per kilogram ($\mu$C/kg). The animals were fasted twelve hours before dosing and for four hours afterward, but otherwise provided with food and water (saline in the case of the cannulated rats) ad libitum.

Through the 72 hour period, after oral administration, an average of 93 percent of the radioactivity was recovered in feces from the normal (non-cannulated) rats. The fecal radioactivity recovery was 89 percent in the cannulated rats; and no significant radioactivity was measured in bile collected from the cannulated rats, indicating that the fecal $^{14}C$ represented unabsorbed compound. No significant radioactivity was detected in expired carbon dioxide or the mesenteric lymph nodes. Urinary $^{14}C$ was negligible (0.013 percent of the dose). Minimal activity (0.032 percent of the dose) was found in the stomach, gastrointestinal tract and rinses, indicating lack of adhesion to or absorption into the gastrointestinal wall. $^{14}C$ was not found in other tissues or the remaining carcasses. The results indicate that the copolymer passed through the gastrointestinal tract without being digested or absorbed through or into the animal tissue.

EXAMPLE 8

Redispersion of Microsuspensions Stabilized by Fatty Acid Soaps

Solutions of the sodium salt of $C_8$ to $C_{16}$ saturated fatty acids, and of oleic acid were first prepared at about 4 percent concentration in water by neutralization of the acid with sodium hydroxide. Sodium stearate solutions were prepared directly from the solid salt. Microsuspensions were prepared to contain about 50 percent of the polymer employed in Example 3B and one percent soap by adding the amount of soap or soap solution listed in the table to 150 g of purified wet cake (about 70 percent polymer) along with the required amount of water to give 50 percent polymer solids. These were then dispersed using a Virtis Mixer (five minutes) and an Eppenbach Homogenizer (15 minutes).

The control was prepared by dispersing the wet cake in deionized water to 50 percent solids with no soap (in the same manner otherwise). This yielded a very thick, pasty suspension. The suspensions dispersed with the soaps gave fluid suspensions except for those containing palmitic or stearic acid soaps, which formed gels upon standing and could be fluidized by agitation.

| Acid | Soap Solution Concentration (Percent) | Soap Solution (Grams) | H₂O (Grams) | Weight Percent Solids |
|---|---|---|---|---|
| Caprylic | 4.16 | 50.48 | 9.52 | 52.5 |
| Capric | 4.19 | 50.12 | 9.88 | 54.5 |
| Lauric | 4.16 | 50.48 | 9.52 | 52.4 |
| Myristic | 4.15 | 50.6 | 9.4 | 52.3 |
| Palmitic | 4.10 | 51.2 | 8.8 | 50.9 |
| Stearic | Solid (100%) | 2.1 | 57.9 | 52.2 |
| Oleic | 4.09 | 51.3 | 8.7 | 53.1 |
| Control (No Soap) | 0 | 0 | 60.0 | 50.0 |

These microsuspensions were tested for efficacy in imbibing fats using the following in vitro test. Six grams of microsuspension was diluted to 25 g with deionized water. This 25 g was added to 125 g 0.1 N HCl and 20 g of palm kernel oil at 37° C. in an 8-ounce glass bottle and hand-shaken 20 times. These were shaken an additional 10 times each 60 seconds thereafter and ratings of both gel consistency and color of the aqueous layer were recorded at various intervals according to the following scales. Microsuspensions treated with soap gave improved (faster) extraction of microsuspension into the fat and/or improved gel times over the control.

| | Time (min) | Gel Rating | Color Rating |
|---|---|---|---|
| Sodium Caprylate | 0.5 | 2 | 2 |
| | 1 | 2 | — |
| | 2 | 2.5 | 4 |
| | 3 | 4 | 4.5 |
| | 4 | 4.5 | 4.5 |
| | 5.5 | 4.5 | 4.5 |
| | 8 | 4.5 | 5 |
| Sodium Caprate | 0.5 | 2 | 2 |
| | 1 | 3 | — |
| | 2 | 3 | 3 |
| | 3 | 5 | 4 |
| | 4 | 5.5 | 4 |
| | 5.5 | 5.75 | 4 |
| | 8 | 5.75 | 4.5 |
| Sodium Laurate | 0.5 | 2 | 4.5 |
| | 1 | — | — |
| | 2 | 2.5 | 4.5 |
| | 3 | 4 | 4.5 |
| | 4 | 5.5 | 5 |
| | 5.5 | 5.75 | 5 |
| Sodium Myristate | 0.5 | 2 | 2 |
| | 1 | 3 | 4 |
| | 2 | 3 | 4.5 |
| | 3 | 5 | 4.5 |
| | 4 | 5.5 | 4.5 |
| | 6 | 5.75 | 4.5 |
| Sodium Palmitate | 0.5 | 2 | 4 |
| | 1.5 | 5 | 4.5 |
| | 3 | 5.75 | 5 |
| | 4 | 5.75 | 5 |
| | 5.5 | 5.75 | 5 |
| Sodium Oleate | 0.33 | 4 | 4.5 |
| | 1 | 5 | 4.5 |
| | 1.75 | 5.75 | 5 |
| | 3 | 5.75 | 5 |
| | 4 | 5.75 | 5 |
| | 5.5 | 5.75 | 5 |
| Sodium Stearate | 0.5 | 2 | 4.5 |
| | 1 | 4 | 4.5 |
| | 1.5 | 5.5 | 5.5 |
| | 2 | 5.75 | 5.5 |
| | 3 | 5.75 | 5.5 |
| | 4 | 5.75 | 5.5 |
| Control | 0.5 | 1 | 1 |
| | 1.5 | 3 | 1 |
| | 3 | 4 | 1 |
| | 4 | 4.5 | 2 |
| | 5.5 | 5 | 2 |
| | 8 | 5.5 | 2 |

Color scale for in vitro test (8-ounce bottle)
1 = 5 g 50 percent microsuspension in 150 g H₂O
2 = 2 g 50 percent microsuspension in 150 g H₂O
3 = 1 g 50 percent microsuspension in 150 g H₂O
4 = 0.5 g 50 percent microsuspension in 150 g H₂O
4.5 = 0.25 g 50 percent microsuspension in 150 g H₂O
5 = opaque gray
5.5 = translucent gray
5.75 = transparent gray
6 = clear
Gel consistency scale for in vitro test
0 = no gel formed
1 = fluid
2 = thickened fluid
3 = soft gel
4 = thickened gel
5 = solid gel - smooth appearance
5.5 = solid gel - irregular surface
5.75 = solid gel - many irregularities on surface

EXAMPLE 9

In Vitro Test of Microsuspension of the Polymer of Example 3B at Various Stages of Purification The tests were performed by adding the specified weight of liquid palm kernel oil to 150 g of a microsuspension at about 1.9 percent polymer concentration. After four hours agitation (20 rpm, end over end in citrate bottles at 37° C.) the samples were examined and a sample of the aqueous layer was taken and assayed for solids by evaporation.

| Appearance of Fat Layer | | | | | | |
|---|---|---|---|---|---|---|
| | Grams Palm Kernel Oil | | | | | |
| | 5 | 10 | 15 | 20 | 25 | 30 |
| No Treatment | C | C− | L | L | L | L |
| Water Washed | C | C | C | C | C− | C− |
| Water and Alcohol Wash | C | C | C | C | C− | C− |

C = Solids
C− = Soft Solid
L = Liquid

| Solids of Aqueous Layer | | | | | | | |
|---|---|---|---|---|---|---|---|
| | Grams Palm Kernel Oil | | | | | | |
| | 0 | 5 | 10 | 15 | 20 | 25 | 30 |
| No Treatment | 1.87 | 1.26 | 1.35 | 1.05 | 0.97 | 1.04 | 1.01 |
| Water Washed | 1.90 | 1.14 | 1.07 | 0.75 | 0.43 | 0.26 | 0.11 |
| Water and Alcohol Wash | 1.85 | 0.80 | 0.61 | 0.52 | 0.05 | 0.0 | 0.0 |

These results show that the two percent hydrophilic stabilizer has an inhibitory effect on the rate of gelation and rate of extraction of polymer solids from the aqueous layer into the fat layer. Removal of stabilizer by either water washing of alcohol washing improves both the extraction rate and gelation rate, both of which are desirable effects. The water wettability and stabilizing effect of the stabilizer, which is needed to stabilize the suspension during polymerization, has undesirable effects when the microsuspension is used, in that the hydrophilic nature of the surface of the polymer particles forces them to stay longer in the aqueous phase. Removing this hydrophilic coating, or treating the surface so that it is hydrophobic, as shown in the examples using fatty acid soaps, improves the extraction and gelation rates.

The data in Examples 10 and 11 was obtained by the procedure of Example 9 using other imbibing polymers as indicated.

EXAMPLE 10

In Vitro Test of 70%/30%/0.05% T-butylstyrene/lauryl Methacrylate/Divinylbenzene Microsuspension

| Grams Palm Kernel Oil | Appearance of Gel | | | Gel Weight Obtained After Filtration (48 hours) |
|---|---|---|---|---|
| | 4 hours | 24 hours | 48 hours | |
| 5 | C | C | C | 9.3 |
| 10 | C | C | C | 17.9 |
| 15 | C | C | C | 26.8 |
| 20 | C− | C | C | 32.6 |
| 25 | L | C | C | 38.3 |
| 30 | L | C | C | 39.8 |

C = Solid
C− = Soft Solid
L = Liquid

EXAMPLE 11

In Vitro Test of 50%/50%/0.5% Isobornyl Methacrylate/Lauryl Methacrylate/Divinylbenzene Microsuspension

| Grams Palm Kernel Oil | Appearance of Gel | | | Gel Weight Obtained After Filtration (48 hours) |
|---|---|---|---|---|
| | 4 hours | 24 hours | 48 hours | |
| 5 | C | C | C | 8.4 |
| 10 | C | C | C | 17.7 |
| 15 | C | C | C | 25.2 |
| 20 | C− | C | C− | 29.8 |
| 25 | L | * | * | 34.0 |
| 30 | L | * | * | 0 |

C = Solid
C− = Soft Solid
L = Liquid
* = Thickened Liquid

EXAMPLE 12

Attempted Extraction of Oil from Preimbibed Polymer-Oil Complex by Sodium Lauryl Sulfate Four samples of imbibed polymer of Example 3B were prepared by shaking 150 g of 2 percent microsuspension with 22.3 g palm kernel oil. The polymer-oil complex was filtered and weighed and then placed into a bottle containing 150 g of sodium lauryl sulfate at the concentrations listed in the table. After shaking at 37° C. for 16 hours, the polymer-oil complex was again filtered and weighed without drying. The results are listed in the following table.

| Sodium Lauryl Sulfate Concentration (Percent) | Initial Oil-Polymer Weight (g) | Final Oil-Polymer Weight (After 16 Hours Shaking) (g) |
|---|---|---|
| 1 | 28.3 | 28.3 |
| 3 | 28.9 | 29.2 |
| 5 | 27.0 | 29.8 |
| 10 | 27.9 | 28.9 |

No weight loss was seen in this experiment indicating that the polymer retains the fat at concentrations of surfactant which can prevent imbibition by unswollen microsuspension. The polymer-fat complex is broken into smaller aggregates by the agitation, but no measurable quantity of fat is extracted. This is analogous to the situation in the body where the microsuspension can imbibe the fat in the stomach, where there are no surfactants and then retain the fats in the polymer when the polymer passes out of the stomach into the duodenum where the bile salts are present and would normally emulsify the fats as part of the normal digestive process.

EXAMPLE 13

In Vitro Tests in Presence of Bile

150 Grams of a 2 percent microsuspension of 5μ beads (70%/30%/0.5% t-butylstyrene/lauryl methacrylate/divinylbenzene) and 20 g palm kernel oil was rotated at 20 rpm (end over end in citrate bottles) for 48 hours at 37° C. and various concentrations of bile salts. At the end of that time, the contents were filtered and weighed. The results are listed in the following table.

| Percent Ox-Bile* | Polymer Fat Gel at 48 hours (g) |
| --- | --- |
| 0 | 33.3 |
| 0.01 | 29.2 |
| 0.03 | 29.4 |
| 0.05 | 29.0 |
| 0.1 | 29.5 |
| 0.3 | 27.2 |
| 0.5 | 24.3 |
| 1 | 8.0 |
| 2 | 2.0 |
| 3 | 1.7 |
| 5 | 1.3 |
| 10 | 1.3 |

*The ox-bile solutions were composed of a 90/10 mixture of ox-bile extract and soybean lecithin made up to the stated concentration.

As shown in the table, the bile salts have very little effect on imbibition of fats at concentrations below 0.5 percent according to these results. The average concentration of bile salts in the duodenum is about 0.4 percent and zero percent in the stomach. Thus, the beads will swell in the stomach and also in those regions of the intestine where the concentration is below 0.5 percent.

An additional sample of polymer-fat gel was prepared similarly but with no ox-bile extract. The polymer-fat gel was filtered and weighed, yielding 26 g of gel. This was placed in a citrate bottle with 150 g of 10 percent ox-bile extract and shaken for 48 hours. The sample was then filtered again and weighed without drying, yielding 28 g of gel. Thus, the gel is not extracted of its fat even at 10 percent bile concentrations, indicating that polymer which imbibes fats in the stomach will retain these at high concentrations of bile salts which it may encounter in the intestinal tract.

Similar experiments by Marsh & Wallace JPL Quart. Tech. Rev., Vol. 2, No. 4, pp. 1–6 (1973) showed that their model bile solutions could extract lipids from polymers. This led them to develop more hydrophilic polymers which would extract the lipids from bile solutions. According to this experiment, that is not necessary with the polymers of this invention.

EXAMPLE 14

Four adult male rhesus monkeys were dosed with the indicated amounts of the polymer of Example 3B along with 6.69 grams of lard, and the percent of dosed lard passing through the gastrointestinal tract at various time intervals was determined. The results were as follows:

| | Monkey | | | | |
| --- | --- | --- | --- | --- | --- |
| | A (%) | B (%) | C (%) | D (%) | Average (%) |
| Control | | | | | |
| 18 hours | 1.8 | 0.7 | 22.8 | 0.2 | 6.4 |
| 42 hours | 5.8 | 12.7 | 51.4 | 2.1 | 18.0 |
| 66 hours | 6.2 | 13.0 | 52.5 | 2.4 | 18.5 |
| 1.5 g Polymer | | | | | |
| 18 hours | 8.1 | 0.7 | 18.5 | 2.8 | 7.5 |
| 42 hours | 29.1 | 5.9 | 29.7 | 17.0 | 20.4 |
| 66 hours | 31.0 | 7.2 | 32.0 | 20.7 | 22.7 |
| 4.5 g Polymer | | | | | |
| 18 hours | 3.1 | 33.2 | 10.9 | 0.5 | 11.9 |
| 42 hours | 23.6 | 51.6 | 35.1 | 11.2 | 30.4 |
| 66 hours | 25.6 | 52.4 | 37.1 | 14.0 | 32.3 |

These results indicate that the polymers are imbibing and retaining the imbibed fat and preventing its absorption by the body.

When five monkeys were dosed with lard preimbibed into the polymer beads at a 5/1 weight to weight ratio, it was found that, on average, 41 percent of the administered lard was recovered while the average recovery of lard when no polymer was employed was only 6.5 percent. Similarly, when the lard and polymer beads are separately but consecutively dosed, the average recovery is about 21 percent, thus indicating that it is critical that conditions for rapid imbibition of the fat by the polymer be created for greater effectiveness.

Results similar to those obtained in the above examples are obtained when employing other pharmacologically-acceptable, solid, particulate, crosslinked, indigestible, fat imbibing, fat retaining polymers such as, for example, styrenic polymers such as, for example, copolymers of vinyl toluene and lauryl methacrylate which have been crosslinked, for example, with divinylbenzene; styrene and lauryl methacrylate which have been crosslinked, for example, with divinylbenzene; styrene and butadiene and various isobornyl methacrylate polymers such as, for example, copolymers of isobornyl methacrylate and lauryl methacrylate which have been crosslinked with divinylbenzene.

What is claimed is:

1. A method of controlling body weight in animals, comprising administering into the gastrointestinal tract of an animal an effective amount of a pharmacologically-acceptable, solid, particulate, crosslinked, indigestible, fat imbibing, fat retaining polymer further characterized in that it swells in liquid lard, contains less than 100 ppm of residual monomer and has a volume average particle diameter of from about 0.05 to about 2000 microns, wherein the polymer is a crosslinked copolymer of an ethylenically unsaturated monomer selected from the group consisting of isobornyl acrylate, isobornyl methacrylate, styrene or alkylstyrene and at least one ester of a $C_8$ to $C_{20}$ fatty alcohol with acrylic or methacrylic acid, crosslinked with a polyethylenically unsaturated crosslinking agent and which polymer imbibes and retains at least a portion of ingested dietary fat when the polymer is administered to the animal in a manner which results in the polymer and ingested dietary fat being in admixture in the gastrointestinal tract, whereby fat is excreted in association with the polymer.

2. The method of claim 1 wherein the polymer particle has a volume when swollen to maximum size with liquefied lard of at least four times the polymer particle's non-swollen volume.

3. The method of claim 2 wherein the polymer is a copolymer of from about 60 to about 85 percent by weight tertiary-alkylstyrene and at least one ester of a $C_8$ to $C_{20}$ fatty alcohol with acrylic or methacrylic acid, crosslinked with from about 0.05 to about 0.1 percent based on the total weight of said tertiary-alkylstyrene and ester of a polyethylenically unsaturated crosslinking agent.

4. The method of claim 3 wherein the tertiary-alkylstyrene is tertiary-butylstyrene.

5. The method of claim 1 wherein the polymer particles have disposed thereon a surfactant which is hydrophobic or which becomes hydrophobic at the pH of the stomach contents.

6. The method of claim 2 wherein the polymer particles have disposed thereon a surfactant which is hydrophobic or which becomes hydrophobic at the pH of the stomach contents.

7. The method of claim 1 wherein the polymer particles have disposed thereon a surfactant which is hydrophobic or which becomes hydrophobic at the pH of the stomach contents and the polymer particles have an unswollen volume average particle size of from about 0.05 to about 20 microns.

8. The method of claim 3 wherein the polymer particles have disposed thereon a surfactant which is hydrophobic or which becomes hydrophobic at the pH of the stomach contents and the polymer particles have an unswollen volume average particle size of from about 0.05 to about 20 microns.

9. The method of claim 4 wherein the polymer particles have disposed thereon a surfactant which is hydrophobic or which becomes hydrophobic at the pH of the stomach contents and the polymer particles have an unswollen volume average particle size of from about 0.05 to about 20 microns.

10. The method of claim 7 wherein the surfactant is a $C_8$ to $C_{18}$ saturated or unsaturated fatty acid salt, polydimethylsiloxane or an acrylic acid polymer.

11. The method of claim 8 wherein the surfactant is a $C_8$ to $C_{18}$ saturated or unsaturated fatty acid salt, polydimethylsiloxane or an acrylic acid polymer.

12. The method of claim 9 wherein the surfactant is a $C_8$ to $C_{18}$ saturated or unsaturated fatty acid salt, polydimethylsiloxane or an acrylic acid polymer.

13. The method of claim 12 wherein the surfactant is sodium stearate.

14. The method of claim 12 wherein the surfactant is polydimethylsiloxane.

15. The method of claim 12 wherein the surfactant is an acrylic acid polymer.

16. The method of claim 1 wherein the crosslinking agent is divinylbenzene.

17. The method of claim 3 wherein the crosslinking agent is divinylbenzene.

18. The method of claim 4 wherein the crosslinking agent is divinylbenzene.

19. The method of claim 3 wherein the tertiary-alkylstyrene is tertiary-butylstyrene and the ester is a $C_8$ to $C_{20}$ methacrylate.

20. The mehod of claim 19 wherein the polymer is a copolymer of tertiary-butylstyrene and lauryl methacrylate.

21. The method of claim 19 wherein the polymer is a copolymer of tertiary-butylstyrene and stearyl methacrylate.

22. The method of claim 19 wherein the polymer is a copolymer of tertiary-butylstyrene and cetyl-eicosyl methacrylate.

23. The method of claim 3 wherein the tertiary-alkylstyrene is tertiary-butylstyrene and the ester is a $C_8$ to $C_{20}$ acrylate.

24. The method of claim 23 wherein the polymer is a copolymer of tertiary-butylstyrene and 2-ethylhexyl acrylate.

25. The method of claim 4 wherein the copolymer contains about 70 percent tertiary-butylstyrene.

26. The method of claim 1 wherein the polymer is a copolymer of isobornyl acrylate and the ester is a $C_8$ to $C_{20}$ methacrylate.

27. The method of claim 26 wherein the polymer is a copolymer of isobornyl acrylate and lauryl methacrylate.

28. The method of claim 26 wherein the polymer is a copolymer of isobornyl acrylate and stearyl mehacrylate.

29. The method of claim 26 wherein the polymer is a copolymer of isobornyl acrylate and cetyl-eicosyl methacrylate.

30. The method of claim 1 wherein the polymer is a copolymer of isobornyl acrylate and the ester is a $C_8$ to $C_{20}$ acrylate.

31. The method of claim 30 wherein the polymer is a copolymer of isobornyl acrylate and 2-ethylhexyl acrylate.

32. The method of claim 1 wherein the polymer is a copolymer of isobornyl methacrylate and the ester is a $C_8$ to $C_{20}$ methacrylate.

33. The method of claim 32 wherein the polymer is a copolymer of isobornyl methacrylate and lauryl methacrylate.

34. The method of claim 32 wherein the polymer is a copolymer of isobornyl methacrylate and stearyl methacrylate.

35. The method of claim 32 wherein the polymer is a copolymer of isobornyl methacrylate and cetyl-eicosyl methacrylate.

36. The method of claim 1 wherein the polymer is a copolymer of isobornyl methacrylate and the ester is a $C_8$ to $C_{20}$ acrylate.

37. The method of claim 36 wherein the polymer is a copolymer of isobornyl methacrylate and 2-ethylhexyl acrylate.

38. The method of claim 1 wherein the polymer particles are administered in the form of an aqueous suspension.

39. The method of claim 3 wherein the polymer particles are administered in the form of an aqueous suspension.

40. The method of claim 4 wherein the polymer particles are administered in the form of an aqueous suspension.

41. The method of claim 1 wherein the polymer is administered from about one hour prior, to about one hour after the time of the ingestion of dietary fat.

42. The method of claim 1 wherein the polymer is in the form of substantially spherical particles with particle diameters of from about 0.05 to about 500 microns.

43. A pharmaceutical composition useful for weight control in animals comprising an effective amount of a pharmacologically-acceptable, solid, particulate, crosslinked, indigestible, fat imbibing, fat retaining polymer further characterized in that it swells in liquid lard, contains less than 100 ppm of residual monomer and has a volume average particle diameter of from about 0.05 to about 2000 microns wherein the polymer is a crosslinked copolymer of an ethylenically unsaturated monomer selected from the group consisting of isobornyl acrylate, isobornyl methacrylate, styrene or alkylstyrene and at least one ester of a $C_8$ to $C_{20}$ fatty alcohol with acrylic or methacrylic acid, crosslinked with a polyethylenically unsaturated crosslinking agent and which polymer imbibes and retains at least a portion of ingested dietary fat when the polymer is administered to the animal in a manner which results in the polymer and ingested dietary fat being in admixture in the gastrointestinal tract, whereby fat is excreted in association with the polymer; and a pharmaceutically-acceptable carrier.

44. The composition of claim 42 wherein the polymer particle has a volume when swollen to maximum size with liquefied lard of at least four times the polymer particle's non-swollen volume.

45. The composition of claim 44 wherein the polymer is a copolymer of from about 60 to about 85 percent by weight tertiary-alkylstyrene and at least one ester of a $C_8$ to $C_{20}$ fatty alcohol with acrylic or methacrylic acid, crosslinked with from about 0.05 to about 0.1 percent based on the total weight of said tertiary-alkylstyrene and ester of a polyethylenically unsaturated crosslinking agent.

46. The composition of claim 45 wherein the tertiary-alkylstyrene is tertiary-butylstyrene.

47. The composition of claim 43 wherein the polymer particles have disposed thereon a surfactant which is hydrophobic or which becomes hydrophobic at the pH of the stomach contents.

48. The composition of claim 44 wherein the polymer particles have disposed thereon a surfactant which is hydrophobic or which becomes hydrophobic at the pH of the stomach contents.

49. The composition of claim 44 wherein the polymer particles have disposed thereon a surfactant which is hydrophobic or which becomes hydrophobic at the pH of the stomach contents and the polymer particles have an unswollen volume average particle size of from about 0.05 to about 20 microns.

50. The composition of claim 45 wherein the polymer particles have disposed thereon a surfactant which is hydrophobic or which becomes hydrophobic at the pH of the stomach contents and the polymer particles have an unswollen volume average particle size of from about 0.05 to about 20 microns.

51. The composition of claim 46 wherein the polymer particles have disposed thereon a surfactant which is hydrophobic or which becomes hydrophobic at the pH of the stomach contents and the polymer particles have an unswollen volume average particle size of from about 0.05 to about 20 microns.

52. The composition of claim 43 wherein the crosslinking agent is divinylbenzene.

53. The composition of claim 45 wherein the crosslinking agent is divinylbenzene.

54. The composition of claim 46 wherein the crosslinking agent is divinylbenzene.

55. The composition of claim 45 wherein the tertiary-alkylstyrene is tertiary-butylstyrene and the ester is a $C_8$ to $C_{20}$ methacrylate.

56. The composition of claim 55 wherein the polymer is a copolymer of tertiary-butylstyrene and lauryl methacrylate.

57. The composition of claim 55 wherein the polymer is a copolymer of tertiary-butylstyrene and stearyl methacrylate.

58. The composition of claim 55 wherein the polymer is a copolymer of tertiary-butylstyrene and cetyl-eicosyl methacrylate.

59. The composition of claim 45 wherein the tertiary-alkylstyrene is tertiary-butylstyrene and the ester is a $C_8$ to $C_{20}$ acrylate.

60. The composition of claim 59 wherein the polymer is a copolymer of tertiary-butylstyrene and 2-ethylhexyl acrylate.

61. The composition of claim 46 wherein the copolymer contains about 70 percent tertiary-butylstyrene.

62. The composition of claim 43 wherein the polymer is a copolymer of isobornyl acrylate and the ester is a $C_8$ to $C_{20}$ methacrylate.

63. The composition of claim 62 wherein the polymer is a copolymer of isobornyl acrylate and lauryl methacrylate.

64. The composition of claim 62 wherein the polymer is a copolymer of isobornyl acrylate and stearyl methacrylate.

65. The composition of claim 62 wherein the polymer is a copolymer of isobornyl acrylate and cetyl-eicosyl methacrylate.

66. The composition of claim 43 wherein the polymer is a copolymer of isobornyl acrylate and the ester is a $C_8$ to $C_{20}$ acrylate.

67. The composition of claim 66 wherein the polymer is a copolymer of isobornyl acrylate and 2-ethylhexyl acrylate.

68. The composition of claim 43 wherein the polymer is a copolymer of isobornyl methacrylate and the ester is a $C_8$ to $C_{20}$ methacrylate.

69. The composition of claim 68 wherein the polymer is a copolymer of isobornyl methacrylate and lauryl methacrylate.

70. The composition of claim 68 wherein the polymer is a copolymer of isobornyl methacrylate and stearyl methacrylate.

71. The composition of claim 68 wherein the polymer is a copolymer of isobornyl methacrylate and cetyl-eicosyl methacrylate.

72. The composition of claim 43 wherein the polymer is a copolymer of isobornyl methacrylate and the ester is a $C_8$ to $C_{20}$ acrylate.

73. The composition of claim 72 wherein the polymer is a copolymer of isobornyl methacrylate and 2-ethylhexyl acrylate.

74. The composition of claim 43 wherein the pharmaceutically-acceptable carrier comprises water and a suspending agent, the composition being in the form of an aqueous suspension adapted for oral administration.

75. The composition of claim 46 wherein the polymer is a copolymer of tertiary-butylstyrene and lauryl methacrylate, crosslinked with divinylbenzene.

76. The composition of claim 75 wherein the polymer is a copolymer of about 70% by weight tertiary-butylstyrene and about 30 percent by weight lauryl methacrylate, crosslinked with about 0.05 to about 0.1 percent by weight divinylbenzene.

77. The composition of claim 76 wherein the polymer comprises from about 10 to about 65 percent by weight of the composition.

78. The composition of claim 43 in the form of a dosage unit adapted for oral administration and comprising from about 250 milligrams to about 60 grams of said polymer per dosage unit.

* * * * *